(12) United States Patent
Van Bladel et al.

(10) Patent No.: US 12,070,404 B1
(45) Date of Patent: Aug. 27, 2024

(54) SELF-EXPANDING VASCULAR FLOW REDUCER WITH STABILIZED THROAT SECTION

(71) Applicant: VahatiCor, Inc., Los Gatos, CA (US)

(72) Inventors: Kevin H. Van Bladel, Livermore, CA (US); Benjamin M. Trapp, Scottsdale, AZ (US); Howard Edelman, San Francisco, CA (US)

(73) Assignee: VahatiCor, Inc., Santa Clara, CA (US)

( * ) Notice: Subject to any disclaimer, the term of this patent is extended or adjusted under 35 U.S.C. 154(b) by 0 days.

(21) Appl. No.: 18/237,603

(22) Filed: Aug. 24, 2023

Related U.S. Application Data (60) Provisional application No. 63/467,233, filed on May 17, 2023.

(51) Int. Cl.
*A61F 2/90* (2013.01)
*A61B 17/12* (2006.01)
*A61F 2/06* (2013.01)
*A61F 2/00* (2006.01)

(52) U.S. Cl.
CPC .......... *A61F 2/90* (2013.01); *A61B 17/12036* (2013.01); *A61B 17/12172* (2013.01); *A61F 2/06* (2013.01); *A61F 2002/0068* (2013.01); *A61F 2210/0014* (2013.01); *A61F 2230/001* (2013.01); *A61F 2230/0078* (2013.01); *A61F 2250/0017* (2013.01); *A61F 2250/0028* (2013.01); *A61F 2250/0039* (2013.01)

(58) Field of Classification Search
CPC ........ A61F 2/88; A61F 2/90; A61F 2230/001; A61F 2250/0039; A61F 2250/0017
See application file for complete search history.

(56) References Cited

U.S. PATENT DOCUMENTS

| | | | | |
|---|---|---|---|---|
| 5,575,818 | A | * 11/1996 | Pinchuk | A61F 2/90 606/195 |
| 8,858,612 | B2 | 10/2014 | Ben-Muvhar et al. | |
| 2003/0040772 | A1 | * 2/2003 | Hyodoh | A61F 2/90 606/200 |
| 2007/0168019 | A1 | * 7/2007 | Amplatz | A61F 2/07 623/1.18 |
| 2016/0206452 | A1 | * 7/2016 | Berez | A61F 2/966 |

FOREIGN PATENT DOCUMENTS

WO 2021226014 A2 11/2021

* cited by examiner

*Primary Examiner* — Rebecca S Preston
(74) *Attorney, Agent, or Firm* — Downs Rachlin Martin PLLC (57) ABSTRACT

Self-expanding implants useful as vascular flow reducers are disclosed with a stabilized throat section to limit the amount of diameter change in certain sections of the implant, for example in the throat section or the center throat ID of an hourglass shape. Methods of making such implants are also described.

30 Claims, 3 Drawing Sheets

FIG. 1

FIG. 2 (detail A)

SELF-EXPANDING VASCULAR FLOW REDUCER WITH STABILIZED THROAT SECTION

RELATED APPLICATIONS

This application claims priority to U.S. Provisional Patent Application No. 63/467,233, filed May 15, 2023, entitled "Self-Expanding Vascular Flow Reducer With Stabilized Throat Section, which is incorporated herein by reference in its entirety.

FIELD

The present disclosure generally relates to vascular flow modulation devices and methods and more specifically to self-expanding vascular flow reducer with stabilized throat section.

BACKGROUND

A coronary sinus reducer is an implantable medical device that can be used in clinically appropriate situations to aid in the management of patients with severe angina symptoms refractory to optimal medical therapy and not amenable to further revascularization. One type of coronary sinus reducer comprises a flow-limiting scaffold providing a restriction within the coronary sinus outflow with the intention of increasing the pressure and/or diverting flow for the purpose of driving higher perfusion to the capillary bed.

Current clinical devices for placement in the coronary sinus generally require a balloon for expansion after delivery to the placement location. One example of a balloon expandable device is the Neovasc Reducer (https://neovasc.com/patients-north-america/#patient_reducer). In some patients, however, expansion of a delivery balloon in the coronary sinus may not be desirable. The present applicant has thus disclosed a number of different self-expanding device designs, for example in International Patent Publication No. WO 2021/226014 by the present Applicant. Self-expanding devices, however, present unique challenges in controlling device geometry over various states of expansion and collapse.

SUMMARY

Embodiments disclosed herein include self-expanding flow reducers, particularly for vascular applications and more specifically useful as coronary sinus reducers, with stabilized throat sections and methods of making same substantially that address challenges in the art and certain disadvantages of prior devices.

In one implementation, the present disclosure is directed to a vascular implant, which includes a self-expanding tubular structure with an hourglass shape; opposed open ends defined by the tubular structure having uncompressed end diameters; and a throat section defined between the opposed open ends and having an uncompressed throat diameter less than the uncompressed end diameters; wherein the throat section is configured such that the throat diameter does not reduce by more than about 35% when the end sections are compressed by up to about 50%.

In another implementation, the present disclosure is directed to an hourglass-shaped self-expanding vascular implant, which includes a plurality of wires braided together to form an open center, compressible and self-expanding structure wherein the wires cross one another at a braid angle; opposed end sections each having an uncompressed end diameter; and a throat section disposed between the end sections having an uncompressed throat diameter less than the uncompressed end diameter, wherein the braid angle between wires disposed in the throat section is less than the braid angle between wires disposed in the end sections by an amount of not more than 40% less.

In yet another implementation, the present disclosure is directed to an hourglass-shaped self-expanding vascular implant, which includes a plurality of wires braided together to form an open center compressible and self-expanding structure wherein the wires cross one another at a braid angle; opposed end sections each having an uncompressed end diameter; and a throat section disposed between the end sections having an uncompressed throat diameter less than the uncompressed end diameter, wherein the braid angle in the throat section is set such that: the throat section diameter does not decrease by more than a predetermined lower limit when the end sections are compressed for fixation of the vascular implant within a vascular lumen; and the throat section is capable of being opened forcibly by radially outward pressure applied within the throat section to a predetermined maximum throat diameter greater than the uncompressed throat diameter.

BRIEF DESCRIPTION OF DRAWINGS

For the purpose of illustrating the disclosure, the drawings show aspects of one or more embodiments of the disclosure. However, it should be understood that the present disclosure is not limited to the precise arrangements and instrumentalities shown in the drawings, wherein.

DETAILED DESCRIPTION

Self-expanding implants useful as vascular flow reducers are disclosed with stabilized throat sections to limit the amount of diameter change in certain sections of the implant, for example in the throat section or the center throat ID of an hourglass shape. Among other advantages of disclosed embodiments is stabilization of the throat ID of such an hourglass-shaped vascular flow reducer after placement within a vascular lumen, such as within the coronary sinus. Among other advantages, stabilization of the throat ID helps to prevent excessive reduction in the throat ID when the hourglass ends are compressed within the vascular lumen after placement. Another advantage is that smaller cell size in the throat section allows for earlier and increased effectiveness of the flow restriction after implantation without the need for covering materials over the mesh structure.

Figure 1:
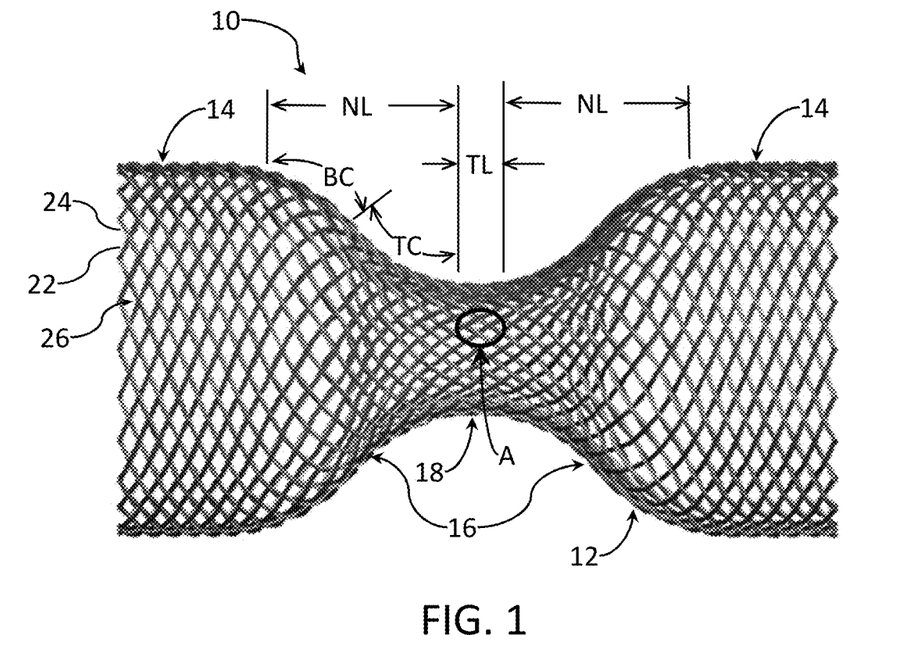
FIG. 1 is a side view of a vascular flow reducer according to an embodiment of the present disclosure.

As shown in FIG. 1, vascular flow reducer 10 comprises an implantable wire mesh construct 12 that is configured to be self-expanding when released from a delivery catheter into the vasculature. Construct 12 includes opposite straight end sections 14, transition sections 16 and throat section 18 at the center. Throat section 18 has a throat length (TL) and transition sections 16 have transition lengths (NL). In some embodiments, the throat length (TL) may be as small as or equal to the pic length (P) (see FIG. 2) and in other embodiments longer throat lengths, such as in the embodiment shown in FIG. 4, may be employed. The transition lengths (NL) of transition braid sections 16 is comprised of two oppositely curved portions, body curve (BC) and throat curve (TC). The transition braid length (NL) can be as short as one cross-over in the center of the device.

Figure 2:
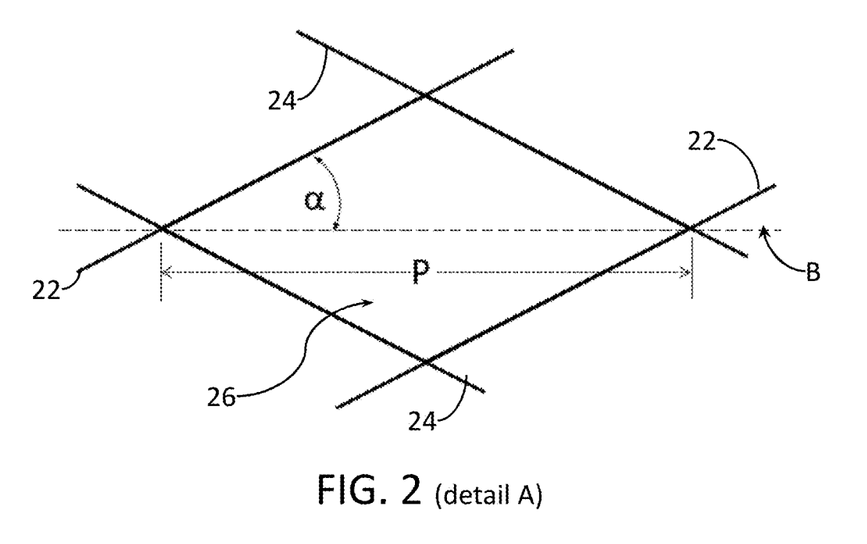
FIG. 2 is a detail view of a single wire mesh cell at detail A of FIG. 1.

Construct 12 is formed as a braided wire mesh with a plurality of crisscrossing wires 22, 24 forming a plurality of open cells 26 between the wires. FIG. 2 shows a detail of one open cell 26 formed between wires 22, 24, which corresponds to detail A in FIG. 1. While the specific relative shape of cells 26 will vary based on their location in construct 12, the basic elements shown in FIG. 1 are consistent throughout different embodiments of the device. As illustrated in FIG. 2, braid angle (a) as defined herein represents the angle between a longitudinal bisecting line (B) through cell 26 and an adjacent wire 22,24. The horizontal distance along line B between the intersection of wires 22, 24 at opposite ends of cell 26 is referred to as the pic length (P).

A challenge in the design of a self-expanding vascular reducer is to ensure that the diameter of the throat section 18 remains constant, at least substantially constant, or at a minimum changes only within acceptable and known limits, when the device 10 is placed in a vessel lumen after compression for delivery and then self-expands to accommodate variations in vessel lumen diameter at the placement site. Another challenge is to provide a device with a throat section 18 that is not overly resistant to later forced expansion in vivo, such as by use of a balloon, in the event that a clinician needs to gain access to the coronary sinus and increase the throat diameter.

It has been determined that these challenges can be met by selective stabilization of the throat section 18, for example, by appropriate selection of the braid angle (a) within the throat section 18. As described herein, increasing braid angle (a) in the throat section de-links changes in the throat section diameter from changes in end section 14 diameter. In general, the greater the throat section braid angle, the lesser the change in throat section diameter in response to changes in the end section diameter. Pic length (P) is also inversely related to braid angle (a) such that increasing the braid angle results in smaller pic lengths, which tightens the weave in the throat section to reduce porosity and increase immediate effectiveness of the flow restriction.

The features, benefits and advantages of embodiments disclosed herein are further illustrated by the following nonlimiting examples (Ex. 1-4). Table I sets forth the dimensions/parameter that are the same for all examples, and Table II sets forth dimensions/parameters that vary between the examples and illustrate further the principles of the present disclosure. In addition to the parameters listed in Table I, each of the example devices is configured with 48 Nitinol wires in a 1 over 2 braid pattern.

TABLE I common parameters, all examples

| Device Overall | | | | Throat Section (TL) | | | End Sections | | | Body Curve | Throat Curve |
|---|---|---|---|---|---|---|---|---|---|---|---|
| Wire Dia. (um) | ID (mm) | OD (mm) | Length (mm) | One pic length (mm) | ID (mm) | OD (mm) | Length (mm) | ID (mm) | Braid angle (α) [°] | pic length (P) [mm] | radius (BC) (mm) | radius (TC) (mm) |
| 140 | 11 | 11.6 | 22.0 | 3.5 | 4.1 | 3.0 | 11 | 72 | 0.5 | 5.4 | 5.0 |

TABLE II example specific parameters

Figure 3:
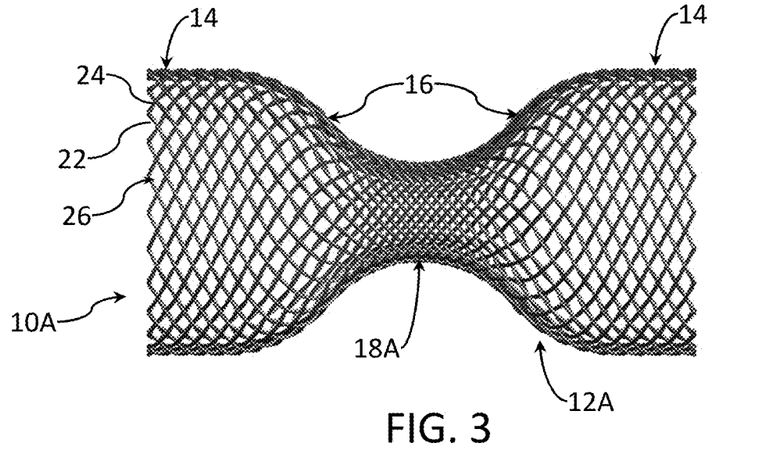
FIG. 3 is a side view of an alternative embodiment of a vascular flow reducer with a higher braid angle in the throat section relative to the embodiment shown in FIG. 1.

| | | A Throat Section braid angle (α) [°] | B Throat Section pic length (P) [mm] | C Throat Section ID under end compression (% Change) | | D Maximum throat ID with forced expansion |
|---|---|---|---|---|---|---|
| Example | Embodiment | | | at 20% compression | at 40% compression | |
| Ex 1 | 10E (FIG. 7) | 17.6 | 1.52 | 2.7 mm (−22%) | 1.8 mm (−49%) | 11 mm (+>200%) |
| Ex 2 | (Not shown) | 25 | 1.10 | 3.3 mm (−6%) | 2.3 mm (−34%) | 9 mm (+~160%) |
| Ex 3 | 10 (FIG. 1) | 32 | 0.79 | 3.4 mm (−3%) | 2.8 mm (−20%) | 6 mm (+~70%) |
| Ex 4 | 10A (FIG. 3) | 52 | 0.39 | ~3.5 mm (~0%) | 3.4 mm (−3%) | 3.5 mm (+~0%) |

Compression of the end sections of the device will occur after deployment because the device will be oversized for the specific vessel into which it is placed so as to ensure security of the device after placement and expansion at the treatment site. For example, the 11 mm devices (11.6 mm OD) described in the examples (Table I), if placed into a vessel with an internal lumen diameter of approximately 9.6 mm, would be 20% oversized before placement, giving rise to 20% compression of the end sections when fully deployed in the vessel. If the same nominally sized device is placed in a vessel with an internal lumen diameter of approximately 8.3 mm, the device would then be 40% oversized before placement and subjected to 40% compression of the end sections when fully deployed in the vessel.

In some embodiments, it is preferable that the throat section ID not reduce by more than 35% when the end sections are subjected to 50% compression. In other embodiments, it is preferable that the throat section ID not reduce by more than 35% when the end sections are subjected to 50% compression. Column C of Table II shows the resulting throat section ID for the example devices and relative reduction in throat section ID under 20% and 40% compression loading conditions. As demonstrated therein, increasing the throat section braid angle in accordance with the present disclosure reduces the amount of throat section ID change over a device oversizing range and variety of use cases. Disclosed embodiments thus address the challenges identified above through use of different braid angles within the throat section of the device. Changing the braid angle allows for the braid to be stabilized in different sections. In the specific design of the hourglass-shaped device, the increased braid angle after shaping stabilizes the throat when the implant is compressed within a vessel.

Stabilization of the throat section with increased braid angle also creates a potential countervailing challenge in some use cases because, as mentioned above, as throat section stability increases with increased braid angle, the ability to forcibly open the throat section in vivo decreases. In situations where forceable opening of the flow restriction may be clinically indicated, it can be accomplished, for example, by placing an appropriately sized balloon or self-expanding stent across the throat section and expanding the balloon or stent within the throat section to expand the throat section radially. The greater stability of the throat section resulting from increase braid angle creates resistance to such forcible opening of the restriction. For example, the Example 1 device 10E (FIG. 7), with a relatively low braid angle ($\alpha$) of 18 degrees in the throat section, can be fully opened to a diameter roughly equal to the end diameters. However, the Example 3 device 10 (FIG. 1), with an increased braid angle ($\alpha$) of 32 degrees, can only be forcibly expanded in the throat section to about 6 mm in an 11 mm overall ID device. The similarly sized Example 4 device 10A (FIG. 3), because of the further increased braid stability afforded by the relatively high 52 degree braid angle ($\alpha$) in the throat section, cannot be forcibly opened under reasonable balloon pressures as would be clinically safe to apply in vivo (generally pressures not greater than about 12 atm). Resistance to forcible opening of the throat section is thus a consideration to be taken into account by persons of ordinary skill when applying the teachings of the present disclosure to configure specific vascular flow reducer devices in accordance herewith.

As will be appreciated by persons skilled in the art based on the teachings of the present disclosure, ideal throat section braid angle to achieve desired performance characteristics will depend upon device dimensions such as throat section size, overall diameter and length, and wire size. In general, devices incorporating the teachings of the present disclosure will have a throat section braid angle in a range selected based on at least two competing parameters: (1) selected such that the throat section internal diameter does not decrease by more than an amount exceeding a functional limit for the specific device application when end sections are compressed by an amount necessary to ensure fixation in the lumen receiving the device, while (2) allowing the throat section to be forcibly opened beyond the nominal throat section internal diameter to a maximum internal diameter as may be dictated by clinical considerations for the specific application, where forcibly opened refers to application of outward radial pressure within the throat section not exceeding a safe level for that specific application. For devices intended for use as coronary sinus reducers, these design parameters translate approximately to (1) a maximum throat section internal diameter decrease of not more than about 20% in response to end section compression of up to about 40%, and (2) a forcibly opened throat section internal diameter increase of at least about 27% in response to internal balloon expansion pressures deemed clinically acceptable for the specific patient by the attending cardiologist, but generally not more than about 12 atm.

Again with respect to coronary sinus reducers, the foregoing design parameters may be achieved with self-expanding constructs ranging in overall internal diameter from about 9 mm to about 15 mm, with throat section internal diameters in the range of about 2.8 mm to about 3.7 mm, and having throat section braid angles in a range of about 29-47 degrees. In some cases more specific configurations with an overall internal diameter in a range of about 10-12 mm, a throat section internal diameter in a range of about 3-3.5 mm will have a throat section braid angle selected in a range of about 31-45 degrees.

Persons of ordinary skill also may derive a variety of techniques for constructing devices according to the present disclosure based on the teachings herein provided. One such technique involves braiding the device onto a shaping mandrel having substantially the same outer dimensions as the desired inner dimensions of the device to be made. For example, the shaping mandrel may be fed directly into the braider (as a core) and the braid angle is set corresponding to the section of the device where the wire is laid down on the shaping mandrel as per the dimensions provided (such as, for example, in the examples listed above). The braid is cinched down onto the shaping mandrel using a cinching wire, for example, silver-plated copper wire. The completed braid on the shaping mandrel is heat set in an oven (following material-specific heat-treating protocols, for example approx. 550 C for 10 mins, followed by quench to cool for the Nitinol wires described above.) The cinching wire is thereafter removed and the braided device thus shaped is removed from the core (shaping mandrel). It should be appreciated that different techniques for removing the core may be devised, such as use of a core that splits in half in the middle of the throat to allow the braid to be removed from the core.

Figure 4:
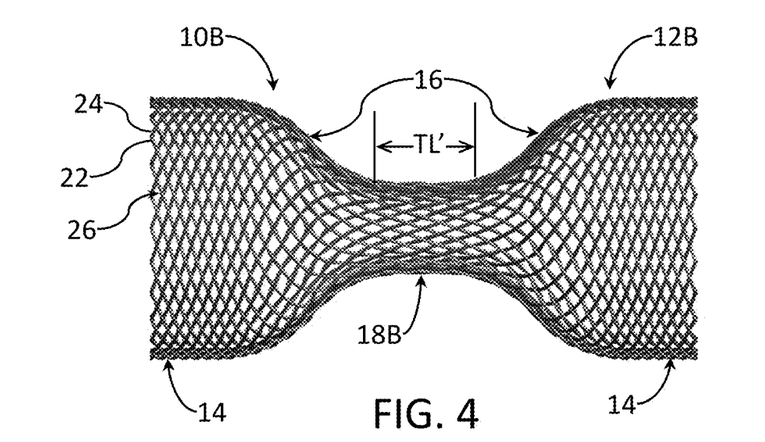
FIG. 4 is a side view of another alternative embodiment of a vascular flow reducer with a longer throat length relative to the embodiments shown in FIGS. 1 and 3.

In other alternative embodiments, the throat section braid angle, length and diameter may be selected according to the teachings of the present disclosure in order to achieve a variety of different performance features for the device thus formed. For example, as shown in FIG. 4, device 10B comprises a wire braided self-expanding construct 12B having end section 14 inside diameters of 11 mm with an extended throat length (TL') in throat section 18B. Braid angle $\alpha$ in the throat section is 32 degrees. As a non-limiting example, extended throat length device 10B may have an increased throat length (TL) in a range of about 2 mm to about 4 mm in an 11 mm device as shown. Extending the throat length may be desirable as a further or alternative parameter to increase throat section stability as described above, and to provide a variety of devices responsive to differing patient anatomies. Extending the throat length extends the number of stabilized higher braid angle cells, which improves the stabilization of the throat ID. In addition, the longer throat increases the flow diversion and pressure drop across the device.

Figure 5:
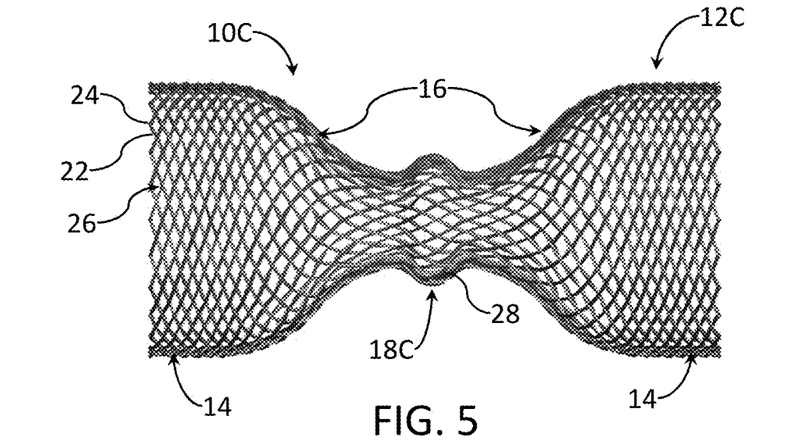
FIG. 5 is a side view of a further alternative embodiment of a vascular flow reducer with a throat curvature.

FIG. 5 illustrates another alternative embodiment of device 10C in which the wire-braided self-expanding construct 12C is formed with a reverse curve section 28 within throat section 18C. A reverse curve section provides a further alternative for adjusting the stability of the throat section to best blend potentially competing parameters of throat stability and amenability to forcible opening in specific device designs adapted to specific clinical needs and patient anatomies. The convex throat changes the stress within the throat and disassociates the load from the two ends of the hourglass from the central throat.

Figure 6:
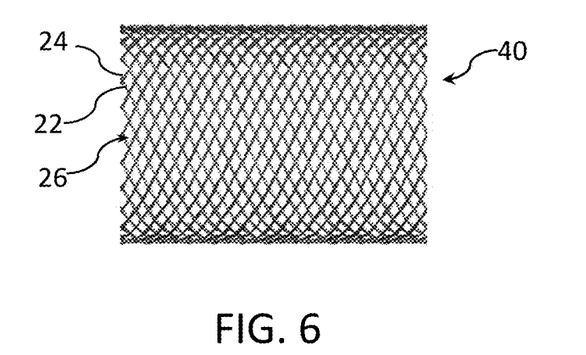
FIG. 6 is a side view of a section of straight mesh tube.
Figure 7:
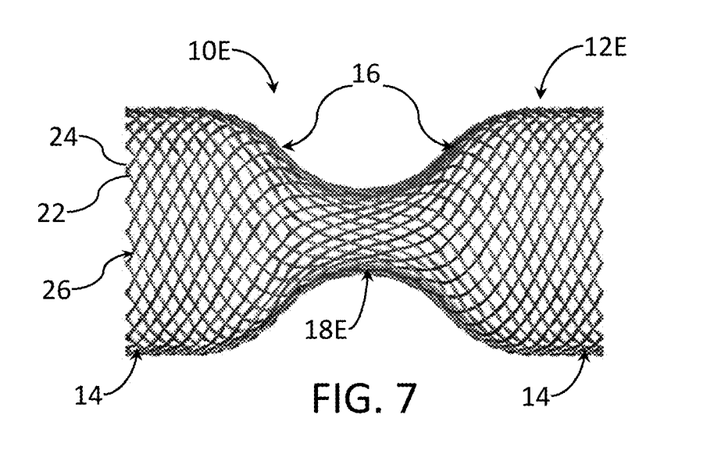
FIG. 7 is a side view of a vascular flow reducer without a stabilized throat section formed from a straight mesh tube section as in FIG. 6.

FIGS. 6 and 7 illustrate device 10E without a stabilized throat section made according to conventional braiding and shape-setting techniques. Device 10E corresponds to Example 1 in Table II. FIG. 6 illustrates a straight braided mesh tube section 40, which is formed into self-expanding construct 12E of device 10E. Tube section 40 is formed on a straight braider configured with 48 Nitinol wires in a 1 over −2 under braid pattern as previously described. However, in this case, braiding is done to form a straight tube section on a 11 mm OD core at a uniform 72 degree braid angle ($\alpha$) throughout. The tube section 40 is then removed from the straight core, cut to length and placed over the shaping mandrel with outer dimensions matching the desired inner dimensions of final device 10E. The tube section is cinched down onto the shaping mandrel using wraps of a cinching wire to form the shape of throat section 18E. The braided Nitinol construct 12E as secured on the shaping mandrel is heat set in an oven at an appropriate time and temperature for the selected braid material (e.g., approximately 550 C for 10 mins, followed by quench to cool). The cinching wire is removed and the braided construct 12E is removed from the shaping mandrel. Using this forming technique with a uniform braid angle in the starting straight tube 40, the final braid angle is dictated by the initial braid angle and degree of shaping. As a result, with this forming technique, there is only limited control over final braid angle ($\alpha$) in throat section 18E. In this specific configuration, the final braid angle ($\alpha$) in the newly shaped throat section 18E is measured at ~18 deg (corresponding to a 1.52 mm pic length). As explained above, this relatively low throat section braid angle may not provide adequate throat section stability in many clinical situations.

Embodiments of self-expanding devices according to the present disclosure also may be described by ratios of specific device parameters including Hourglass Ratio, Braid Angle Ratio and Shape Set Ratio. These parameters are explained, defined and applied below.

Hourglass Ratio refers to the ratio of device end diameter to device throat diameter. A straight tube would thus have an hourglass ratio of 1.0. Self-expanding vascular devices according to the present disclosure have an hourglass ratio of 1.8 or greater.

Initial Braid Angle is the uniform braid angle of an unstabilized straight tube from which an hourglass-shaped device may be formed by shape setting. An example is shown in FIG. 6. Initial Braid Angle also corresponds to the end section braid angle in both stabilized and unstabilized devices according to the present disclosure.

Shape Set Angle is the braid angle in the throat section of an unstabilized device after shape setting to the desired reduced diameter throat section. Shape Set Angle as used herein refers only to the braid angle in the throat section of unstabilized devices as exemplified by device 10E in FIG. 7. It should be noted that regardless of whether or not a specific device has a stabilized throat section as taught herein, a theoretical Shape Set Angle as defined above can be determined for any device. To determine Shape Set Angle empirically, a straight braided tube having the same configuration and braid angle as the end sections of the device under consideration is placed on a shaped mandrel and shape set to have the final throat section diameter as the device under consideration. The throat section braid angle resulting from the shape setting of the straight uniform tube under these conditions is the Shape Set Angle. Shape Set Angle can also be calculated for any device using the following formula [1]:

sin(Shape Set Angle)=Diameter Throat/Diameter End*sin(Initial Braid Angle)           [1]

The Shape Set Angle for a number of different size devices (all with a 72 degree Initial Braid Angle) are shown in Table III:

TABLE III

Shape Set Angles (in degrees)
(72 degree Initial Braid Angle)

| ↓ End Diameter | Throat Diameter → | | | |
|---|---|---|---|---|
| | 5 mm | 4 mm | 3.5 mm | 3 mm |
| 9 mm | 31.9 | 25 | 21.7 | 18.5 |
| 11 mm | 25.6 | 20.2 | 17.6 | 15 |
| 13 mm | 21.5 | 17 | 14.8 | 12.7 |
| 15 mm | 18.5 | 14.7 | 12.8 | 11 |

Shape Set Ratio refers to the ratio of the Initial Braid Angle to the Shape Set Angle. For example, device 10E has an initial braid angle of 72 degrees (equal to the end section braid angle as shown in Table I) and a shape set braid angle of 17.6 degrees (as shown in Table II), giving a Shape Set Ratio of 72/17.6=4.1.

Shape Set Ratios for the examples listed in Table III are given in Table IV:

TABLE IV

Shape Set Ratios for Table III Examples

| ↓ End Diameter | Throat Diameter → | | | |
|---|---|---|---|---|
| | 5 mm | 4 mm | 3.5 mm | 3 mm |
| 9 mm | 2.3 | 2.9 | 3.3 | 3.9 |
| 11 mm | 2.8 | 3.6 | 4.1 | 4.8 |
| 13 mm | 3.4 | 4.2 | 4.9 | 5.7 |
| 15 mm | 3.9 | 4.9 | 5.6 | 6.6 |

Braid Angle Ratio refers to the ratio of the actual braid angle in the throat section to the actual braid angle in the end sections for the device. Devices with a stabilized throat section according to the present disclosure will have a Braid Angle Ratio that is less than the Shape Set Ratio for the same device. Braid Angle Ratios compared to Shape Set Ratios for Examples 1-4 in Tables I and II are presented in Table V:

TABLE V

Braid Angle Ratio vs. Shape Set Ratio

| Example | Embodiment | Braid Angle Ratio | Shape Set Ratio | Stabilized |
|---|---|---|---|---|
| Ex 1 | 10E (FIG. 7) | 4.1 | 4.1 | NO |
| Ex 2 | (not shown) | 2.88 | 4.1 | YES |
| Ex 3 | 10 (FIG. 1) | 2.25 | 4.1 | YES |
| Ex 4 | 10A (FIG. 3) | 1.38 | 4.1 | YES |

Embodiments disclosed herein include hourglass-shaped, self-expanding, wire-braided devices having an Hourglass Ratio of 1.8 or greater and a Braid Angle Ratio that is lower than the Shape Set Ratio for the device.

Embodiments disclosed herein further include hourglass-shaped, self-expanding, wire-braided devices having an Hourglass Ratio of 1.8 or greater and a throat section braid angle within a range of about 31 to 45 degrees.

Embodiments disclosed herein also include hourglass-shaped, self-expanding, wire-braided devices having an Hourglass Ratio of 1.8 or greater and a throat section that cannot be forcibly expanded to beyond a diameter of 89% of the device end section diameter under application of up to 12 atm of radial expansion pressure applied within the throat section.

In certain embodiments, the self-expanding tubular structures disclosed herein are configured such that compression of the structure to a reduced overall diameter at least 50% less than the uncompressed end diameter can occur without substantial plastic deformation of the self-expanding tubular structure. In some embodiments, a failure of the self-expanding tubular structure to return to at least 90% of the original uncompressed end diameter would evidence a substantial plastic deformation.

Further features, advantages, and benefits of embodiments disclosed herein include one or more of the following:

Improvement in the throat ID of an hourglass-shaped device when the device is constrained within a vessel.

Increased braid angle in a section of a braid to improve the stability of the diameter when constrained.

Improved throat diameter in the oversizing range.

Variable braid angle along the length of a device to improve properties and prevent ID effected by the two ends of the device.

An implant that is self-expanding made of nitinol material in the shape of an hourglass.

The design is a closed braided construction.

The braid angle is controllable to ensure robust radial force at the ends of the device.

The braid angle can be designed so that it has a different braid angle at the two ends and has an increased braid angle in the middle section.

The increased braid angle in the middle provides stabilization of the throat and improved performance when the two ends are constrained.

The change in braid angle provides a discontinuity between the ends and the middle of the braid such that it does not compress the same degree when the braid was all the same braid angle.

The implant depending on the braid angle can be forcibly opened to a certain predictable diameter after implantation when required by clinical needs such as thrombus formation in the throat section or to allow for a follow-up procedure such as an ICD or CRT lead if necessary.

The implant is configurable to balance the ability to forcibly open the throat section with the ability to maintain throat ID over a range of specific oversizing requirements.

In one exemplary design, the device is based on 15-50% oversizing with a 3.0 mm throat ID that is capable of being forcibly opened to 4.5 mm.

The foregoing has been a detailed description of illustrative embodiments of the disclosure. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure or of the inventions as set forth in following claims.

What is claimed is:

1. A vascular flow-reducing implant, comprising:
   a self-expanding tubular structure configured to form a flow reducing restriction when self-expanded within a vascular lumen;
   opposed open end sections defined by the tubular structure having uncompressed end diameters; and
   a throat section forming said flow-reducing restriction defined between the opposed open end sections and having an uncompressed throat diameter less than the uncompressed end diameters;
   wherein the throat section is configured such that the throat diameter does not reduce by more than about 35% when the end sections are compressed by up to about 50%.

2. The vascular implant of claim 1, wherein the throat section is configured such that the throat diameter does not reduce by more than about 34% when the end sections are compressed by up to about 40%.

3. The vascular implant of claim 1, wherein the throat section is further configured such that the throat diameter does not reduce by more than about 6% when the end sections are compressed by not more than about 20%.

4. The vascular implant of claim 1, wherein:
   said self-expanding tubular structure is a braided wire tubular structure formed by a plurality of braided wires intersecting at braid angles; and
   the braid angles between wire portions disposed in the throat section are less than braid angles between wire portions disposed in the end sections.

5. The vascular implant of claim 4, wherein:
   the uncompressed end diameters are in a range from about 9 mm to about 15 mm;
   the uncompressed throat diameter is in a range from about 2.8 mm to about 3.7 mm; and
   the throat section braid angle is in a range of about 29-47 degrees.

6. The vascular implant of claim 5, wherein:
   the uncompressed throat diameter is in a range of about 3-3.5 mm; and the throat section braid angle is in a range of about 31-45 degrees.

7. The vascular implant of claim 4, wherein:
the self-expanding tubular structure has an Hourglass Ratio, a Braid Angle Ratio and a Shape Set Braid Ratio;
the Hourglass Ratio is greater than 1.8; and
the Braid Angle Ratio is lower than the Shape Set Braid Ratio.

8. The vascular implant of claim 4, wherein the self-expanding tubular structure is configured with:
an Hourglass Ratio greater than 1.8; and
the braid angle in the throat section is 32 degrees or larger.

9. The vascular implant of claim 8, wherein the braid angle in the throat section is not greater than 45 degrees.

10. The vascular implant of claim 4, wherein:
the self-expanding tubular structure is formed in an hourglass shape with a transition section between each end section and the throat section;
the transition sections each have two oppositely curved portions; and
the oppositely curved portions comprise an outer body curve and an inner throat curve, said outer body curve having a radius of curvature greater than a radius of curvature of the inner throat curve.

11. The vascular implant of claim 10, wherein the radius of curvature of the outer body curve is about 5.4 mm and the radius of curvature of the inner throat curve is about 5.0 mm.

12. The vascular implant of claim 11, wherein the end sections have an inner diameter of about 11 mm.

13. The vascular implant of claim 1, wherein:
the self-expanding tubular structure has an Hourglass Ratio greater than 1.8;
the self-expanding tubular structure has uncompressed end diameters greater than 6 mm; and
the throat section diameter cannot be forcibly opened by application of outward radial pressure within the throat section to a forced open diameter of more than 89% of the uncompressed end diameters.

14. The vascular implant of claim 13, wherein the outward radial pressure is not more than about 12 atm.

15. The vascular implant of claim 1, wherein the throat section has a length of about 2 mm to about 4 mm.

16. The vascular implant of claim 1, wherein the throat section includes a reverse curve section with a diameter greater than the uncompressed throat diameter.

17. The vascular implant of claim 1, wherein the self-expanding tubular structure is compressible to a reduced overall diameter at least 50% less than the uncompressed end diameters without substantial plastic deformation of said self-expanding tubular structure.

18. The vascular implant of claim 1, wherein the uncompressed throat diameter is selected to provide a flow restriction of predetermined minimum size within a predetermined range of expansion of the end sections when said vascular implant is placed within a vascular lumen.

19. The vascular implant of claim 18, wherein the self-expanding tubular structure has an Hourglass Ratio in a range of about 2.4 to about 5.4.

20. A vascular implant, comprising
a self-expanding tubular structure with an hourglass shape;
opposed open end sections defined by the tubular structure having uncompressed end diameters; and
a throat section defined between the opposed open end sections and having an uncompressed throat diameter less than the uncompressed end diameters;
wherein the throat section is configured such that the throat diameter does not reduce by more than about 35% when the end sections are compressed by up to about 50%;
wherein said self-expanding tubular structure is a braided wire tubular structure formed by a plurality of braided wires intersecting at braid angles, and the braid angles between wire portions disposed in the throat section are less than braid angles between wire portions disposed in the end sections; and
wherein the intersecting wires form open cells therebetween with open cells disposed in the throat section being smaller than open cells in the end sections.

21. An hourglass-shaped self-expanding vascular implant, comprising:
a plurality of wires braided together to form an open center, compressible and self-expanding structure wherein the wires cross one another at a braid angle;
opposed end sections each having an uncompressed end diameter; and
a throat section disposed between the end sections having an uncompressed throat diameter less than the uncompressed end diameter, wherein the braid angle between wires disposed in the throat section is less than the braid angle between wires disposed in the end sections by an amount of not more than 40% less.

22. The vascular implant of claim 21, wherein:
said implant has an Hourglass Ratio of about 2.4 to about 5.4;
the uncompressed end diameter is greater than 6 mm; and
the throat section cannot be forcibly opened by application of outward radial pressure within the throat section to a forced open diameter of more than 89% of the uncompressed end diameter.

23. The vascular implant of claim 22, wherein the outward radial pressure is not more than about 12 atm.

24. The vascular implant of claim 21, wherein:
the hourglass-shape comprises transition sections disposed between the end sections and the throat section, wherein the transition sections each have two oppositely curved portions;
the compressible and self-expanding structure has an Hourglass Ratio, a Braid Angle Ratio and a Shape Set Braid Ratio;
the Hourglass Ratio is greater than 1.8; and
the Braid Angle Ratio is lower than the Shape Set Braid Ratio.

25. The vascular implant of claim 21, wherein:
the hourglass-shape comprises transition sections disposed between the end sections and the throat section, wherein the transition sections each have two oppositely curved portions;
said implant is configured with an Hourglass Ratio greater than 1.8; and
the braid angle in the throat section is greater than 32 degrees.

26. An hourglass-shaped self-expanding vascular implant, comprising:
a plurality of wires braided together to form an open center compressible and self-expanding hourglass-shaped structure wherein the wires cross one another at a braid angle;
opposed end sections each having an uncompressed end diameter; and
a reinforced throat section disposed between the end sections having an uncompressed throat diameter less than the uncompressed end diameter with an Hourglass Ratio of about 2.4 to about 5.4;

wherein the braid angle in the throat section is set such that:

the throat section diameter does not decrease by more than a predetermined lower limit when the end sections are compressed for fixation of the vascular implant within a vascular lumen; and with the end sections compressed for fixation with the vascular lumen, the throat section is capable of being opened forcibly by radially outward pressure applied within the throat section to a predetermined maximum throat diameter greater than the uncompressed throat diameter.

27. The vascular implant of claim 26, wherein the predetermined lower limit of the throat section diameter decrease is more than about 20% of the uncompressed throat diameter in response to end section compression of up to about 40%.

28. The vascular implant of claim 26, wherein said vascular implant is configured as a coronary sinus flow reducer with a throat section diameter selected to create a predetermined flow restriction within the coronary sinus and the predetermined maximum throat diameter is at least about 27% greater than the uncompressed throat diameter.

29. The vascular implant of claim 28, wherein the hourglass-shaped structure comprises transition sections disposed between the end sections and the throat section, wherein the transition sections each have two oppositely curved portions.

30. The vascular implant of claim 26, wherein the outward radial pressure required to open the throat section does not exceed 12 atm.

* * * * *